United States Patent [19]
Sikic et al.

[11] Patent Number: 5,830,697
[45] Date of Patent: Nov. 3, 1998

[54] P-GLYCOPROTEIN MUTANT RESISTANT TO CYCLOSPORIN MODULATION

[75] Inventors: Branimir I. Sikic, Stanford; Gang Chen, Palo Alto, both of Calif.

[73] Assignee: The Board of Trustees of the Leland Stanford Junior University, Palo Alto, Calif.

[21] Appl. No.: 784,649

[22] Filed: Jan. 21, 1997

[51] Int. Cl.$^6$ .............................. C12P 21/06; C12N 5/22; C12N 15/12; C07K 14/435
[52] U.S. Cl. ..................... 435/69.1; 435/325; 435/366; 435/372; 536/23.5; 530/350
[58] Field of Search ..................................... 435/69.1, 325, 435/366, 372, 320.1; 536/23.5; 530/350

[56] References Cited

PUBLICATIONS

Loo et al. J. Biol. Chem. 268: 19965–19972 1993.
Chen et al Proc. Am. Assoc. Cancer Res 37:323 Mar. 1996.
DuMontet et al Proc. Am Assoc. Cancer Res 37:329 Mar. 1996.

*Primary Examiner*—Karen C. Carlson
*Attorney, Agent, or Firm*—Pamela J. Sherwood; Bozicevic & Reed LLP

[57] ABSTRACT

A mutated form of human P-glycoprotein (mdr1ΔF335/336) is identified, consisting of a single or double codon deletion (Phe335 and/or 336) in the TM region of P-gp. The mdr1ΔF335/336 encoded P-glycoprotein is characterized by an altered spectrum of cross-reactivity to cytotoxins and resistance to modulation by cyclosporins, with a loss of the capacity to bind or transport cyclosporine, PSC 833, and vinblastine. These data demonstrate that cyclosporine, PSC 833, vinblastine, Rh-123, and dactinomycin share at least one binding domain on, which plays an important role in the interaction of P-gp with modulators. The nucleic acid compositions encoding mdr1ΔF335/336 find use in gene therapy to transfer modulator-resistant multidrug resistance into transfected cells; to produce the encoded protein for functional mapping studies, and in studying associated physiological pathways.

9 Claims, No Drawings

P-GLYCOPROTEIN MUTANT RESISTANT TO CYCLOSPORIN MODULATION

STATEMENT AS TO FEDERALLY SPONSORED RESEARCH

This invention was made with government support from the National Institutes of Health grant RO1 CA52168. The Government may have certain rights to this invention.

BACKGROUND OF THE INVENTION

The development of drug resistance in tumor cells is a major obstacle to achieving a clinical response in cancer chemotherapy. A frequently observed mechanism for multidrug resistance (MDR) is increased expression of the membrane transporter P-glycoprotein (P-gp), which is an ATP-dependent drug efflux pump of broad substrate specificity. The mdr1 gene, which encodes P-gp, is expressed in some normal and malignant tissues and has been associated with a poor prognosis in several types of cancer.

Cyclosporin, its analogue PSC 833 (PSC), verapamil and other P-glycoprotein modulators have been shown to increase cellular drug accumulation and reverse MDR through competitive binding to P-gp. The outcome of chemotherapy against MDR tumors may be improved by including the administration of P-gp inhibitors in treatment. As is the case with most cytotoxic therapies, however, selection for drug resistant mutants may occur.

Conversely, genes that confer specific drug resistance can be very useful. Expression of resistance genes allows the targeted cell types to withstand otherwise toxic levels of a drug. For example, in the treatment of advanced cancer patients, the practicing oncologist must reach a balance between providing a therapy that is sufficient to kill the tumor cells, but which will not severely damage the patient's hematopoietic system. Damage to hematopoietic progenitor cells results in risk for severe infection and bleeding, and limits the doses of chemotherapy. Introduction of specific resistance into hematopoietic stem cells would reduce the risks and facilitate optimal dosing of chemotherapy.

Reversal of MDR by modulators such as PSC833 may improve the efficacy of cancer chemotherapy, but cannot be combined with the approach of transferring the mdr1 gene into normal bone marrow cells, since PSC833 would counteract the protective effects of the mdr1 gene. Methods of circumventing this impasse are of interest.

Relevant Literature

Keller et al. (1992) Int J Cancer 50:593–7 describe the P-glycoprotein inhibitor PSC388. Resistance to verapamil in a multi-drug-resistant human multiple myeloma cell line is described in Abbaszadegan et al. (1996) Int. J. Cancer 66:506–514. A resistant cell line derived by selection in doxorubicin and verapamil was shown to have altered the intracellular location of P-glycoprotein. Hypersensitivity to cyclosporin A in mouse cells selected with PSC388 was demonstrated by Didier and Loor (1995) Int J Cancer 63:263–267.

Pharmacologic implications for the clinical use of P-glycoprotein inhibitors is discussed in Lum and Gosland (1995) The Hematol Oncol Clin North Am 9:319–336. Many modulators of MDR lead to alterations of tissue function and enhance toxicity to normal tissue at clinically relevant doses. In vitro data suggest many MDR modulators will enhance hematologic toxicity, beyond that predicted by the increased exposure from pharmacokinetic effects. The pharmacokinetics of daunomycin retention in MDR cells in the presence of different P-glycoprotein inhibitors is shown in Boesch and Loor (1994) Anticancer Drugs 5:229–238.

Cardarelli et al. (1995) Cancer Res 55:1086–1091 explore the substrate specificity of the MDR1 gene product with a point mutation at amino acid residue 185 in which valine is substituted for glycine. The mutant (V185) conferred increased resistance to colchicine. This MDR phenotype in both in both wild-type and mutant transfected cells was overcome by the addition of cyclosporin A, quinidine, or verapamil. Kajiji et al. (1994) Biochemistry 33:5041–8 describe P-glycoprotein mutations in predicted transmembrane (TM) domain 11 (ser941).

DATABASE REFERENCES FOR NUCLEOTIDE AND AMINO ACID SEQUENCES

Chen et al. (1986) Cell 47:381–389 provides the complete cDNA sequence encoding wild-type human p-glycoprotein. The sequence has the Genbank accession number M14758.

SUMMARY OF THE INVENTION

Isolated nucleic acid compositions encoding a mutated form of human P-glycoprotein (mdr1ΔF335/336) are provided. The mdr1ΔF335/336 encoded P-glycoprotein is characterized by an altered spectrum of cross-reactivity to cytotoxins and resistance to modulation by cyclosporins. The nucleic acid compositions find use in gene therapy to transfer modulator-resistant multidrug resistance into transfected cells; to produce the encoded protein for functional mapping studies, and in studying associated physiological pathways. Modulation of the gene activity in vivo is useful for therapeutic purposes.

DESCRIPTION OF THE PREFERRED EMBODIMENTS

A mutated form of human P-glycoprotein (mdr1ΔF335/336) that is resistant to cyclosporin modulation, and its encoding nucleic acid sequence, is provided. The mdr1ΔF335/336 has a deletion at position 335 or 336 or both, in the transmembrane 6 region. Modulation of the mdr1ΔF335/336 gene activity in vivo is useful for therapeutic purposes, allowing the transfer of the resistant phenotype into cells, particularly hematopoietic cells, that are sensitive to cyclosporin modulators. The mdr1ΔF335/336 mutant is useful in drug screening assays to investigate the effects of modulator binding on P-glycoprotein mediated drug efflux.

Unless otherwise stated, mdr1ΔF335/336 protein shall be intended to mean a polypeptide having the amino acid sequence of (SEQ ID NO:2). The invention further includes variants of SEQ ID NO:2 that have a double deletion of F335 and F336; and variants that have 80% or greater sequence homology to SEQ ID NO:2 and that maintain the biological function of SEQ ID NO:2 in terms of resistance to cyclosporin inhibition of the multidrug transport activity. The mdr1ΔF335/336 variant was derived by co-selection of an mdr1 expressing cell line with doxorubicin and the cyclosporin D analogue PSC 833, a potent inhibitor of the multidrug transporter P-glycoprotein. The variant confers decreased cross-resistance to vinca alkaloids and no resistance to dactinomycin, while resistance to doxorubicin and paclitaxel is retained, as well as substantial cross-resistance to etoposide. The multidrug resistant phenotype is not modulated by PSC 833 or cyclosporin A. These data demonstrate that Phe335/336 is an important binding site on P-glycoprotein for substrates such as dactinomycin and Vinca alkaloids, and inhibitors such as cyclosporin and its analogue PSC 833.

The mdr1ΔF335 gene (SEQ ID NO:1) or mdr1ΔF336 gene (SEQ ID NO:5) has a 3837 nt open reading frame encoding a protein of 1279 amino acids (SEQ ID NO:2). The amino acid sequence differs from the wild-type sequence by a deletion of the phenylalanine normally found at residue 335 or 336. The term "mdr1ΔF335/336 gene" as used herein shall be intended to mean the open reading frame encoding the specific P-gp polypeptide of SEQ ID NO:2. Also included are homologs of the gene that encode a protein having substantially the same resistance to cyclosporin modulation and activity as a transporter.

The mdr1ΔF335/336 gene is isolated and obtained in substantial purity, generally as other than an intact mammalian chromosome. Usually, the DNA will be obtained substantially free of other nucleic acid sequences that do not include an mdr1ΔF335/336 gene sequence or fragment thereof, generally being at least about 50%, usually at least about 90% pure and is typically "recombinant", i.e. flanked by one or more nucleotides with which it is not normally associated on a naturally occurring chromosome.

For use as a hybridization probe or for heteroduplex analysis, fragments of the mdr1ΔF335/336 gene that encompass the deletion at residue 335/336 may be used. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt.

The mdr1ΔF335/336 gene may be employed for producing cyclosporin resistant P-glycoprotein. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

Modification of Cells with mdr1ΔF335/336

The mdr1ΔF335/336 gene is used to confer multiple drug resistance to target mammalian cells, particularly human cells, used in gene therapy. The mdr1ΔF335/336 gene may be used alone, or in combination with other therapeutic genes, e.g. adenosine deaminase, cytokine genes, immunoglobulin or T cell receptors or synthetically produced variations thereof, genes that correct genetic defects, such as dystrophin, CFTR, etc. The constructs will normally include a marker that allows for selection of cells into which the construct has been incorporated. The mdr1ΔF335/336 gene may be used as a selectable marker, or other markers known in the art, such as resistance to G418, hygromycin, and the like may be used. Less conveniently, negative selection is used, where the marker is the HSV-tk gene, which will make the cells sensitive to agents, such as acyclovir and gancyclovir.

Cells of interest as targets include myoblasts; fibroblasts; keratinocytes; adrenal cells; hepatic cells; epithelial cells, particularly those found in the oral cavity or gastrointestinal tract; endothelial cells; osteoblasts; chondrocytes; lymphoid, myeloid and pluripotential hematopoietic cells, particularly hematopoietic stem cells having long term reconstitution ability (for example, see U.S. Pat. No. 5,061,620, herein incorporated by reference). Human hematopoietic stem cells are conveniently characterized by their expression of cell surface molecules, and have been reported to express CD34, Thy-1 and c-kit, while lacking expression of a number of markers associated with lineage committed cells, e.g. CD3, CD4, CD8, CD14, CD15, MAC-1, etc.

Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are hematopoietic stem cells. For example, see Schwarzenberger et al. (1996) Blood 87:472–478; Nolta et al. (1996) P.N.A.S. 93:2414–2419; and Maze et al. (1996) P.N.A.S. 93:206–210.

Combinations of retroviruses and an appropriate packaging line may be used, where the capsid proteins will be functional for infecting the target cells.

Usually, the cells and virus will be incubated for at least about 24 hours in the culture medium. The cells are then allowed to grow in the culture medium for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392–8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) *Mol. Cell. Biol.* 5:431–437); PA317 (Miller et al. (1986) *Mol. Cell. Biol.* 6:2895–2902) GRIP (Danos et al. (1988) *PNAS* 85:6460–6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the mdr1ΔF335/336 gene after integration into a target cell genome. For some uses, however, it is desirable to have a regulatable promoter driving expression of mdr1ΔF335/336. Where such a promoter is included, the promoter function of the LTR will be inactivated. This is accomplished by a deletion of the U3 region in the 3'LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL–2 promoter in T cells, immunoglobulin promoter in B cells, etc.

Hematopoietic stem cells expressing the mdr1ΔF335/336 gene are useful, for example, in cancer therapy. In many situations the therapy involves removal of bone marrow or other source of stem cells from a human host, isolating the stem cells from the source and expanding the stem cells. Meanwhile, the host is treated to substantially or completely ablate native hematopoietic capability. After completion of the treatment of the host, the modified stem cells may then be restored to the host. Allogeneic or autologous stem cells carrying the subject mdr1 gene may also be used throughout the ablative treatment, as the cells will be relatively resistant to cytotoxins.

To prove that one has genetically modified stem cells, various techniques may be employed. The genome of the cells may be restricted and used with or without amplification. The polymerase chain reaction; gel electrophoresis; restriction analysis; Southern, northern, and western blots; sequencing; or the like, may all be employed. The cells may be grown under various conditions to ensure that the cells are capable of maturation to all of the hematopoietic lineages while maintaining the ability to express the introduced DNA. Various tests in vitro and in vivo may be employed to ensure that the pluripotent capability of the stem cells has been maintained.

The stem cells may be administered in any physiologically acceptable medium, normally intravascularly, although they may also be introduced into bone or other convenient site, where the cells may find an appropriate site for regeneration and differentiation. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with stem cell proliferation and differentiation.

Uses of mdr1ΔF335/336 Protein

The mdr1ΔF335/336 protein is made available in large amounts by employing an expression host. The protein can be isolated and purified using conventional methodologies. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as cellular debris.

The polypeptide is useful for the production of antibodies, where short fragments provide for antibodies specific for the F335/336 deletion, and larger fragments or the entire protein allow for the production of antibodies over the surface of the polypeptide. Antibodies may be raised to isolated peptides or to the native protein, e.g. by immunization with cells expressing mdr1ΔF335/336, immunization with liposomes having P-glycoprotein inserted in the membrane, etc. Antibodies that recognize the F335/336 deletion are particularly useful.

Antibodies are prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains may be mixed to further enhance the affinity of the antibody.

By providing for the production of large amounts of ΔF335/336 P-gp, one can identify ligands or substrates that bind to or modulate the biological activity. The transport function, and its inhibition by modulators such as cyclosporin are of interest. Areas of investigation include the development of cancer treatments, adverse effects of currently available therapies, etc.

Of particular interest are screening assays for inhibitors that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transporter function, etc.

Uses of the Gene

The DNA sequences are used in a variety of ways. They may be used as probes for identifying genes having the subject mutation. The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose and then probed with a fragment of the subject DNA as a probe. Other techniques may also find use. Detection of mRNA having the subject sequence is indicative of P-gp gene expression in the sample.

For use as a hybridization probe, nucleotide analogs having improved biological stability or hybridization kinetics may be preferred. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O- methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

A number of methods are available for analyzing DNA sequences. The F335/336 region may be cloned into a suitable vector and grown in sufficient quantity for analysis, or amplified by conventional techniques, such as the polymerase chain reaction (PCR). The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2–14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine(TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal P-gp sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences.

The following examples are put forth so as to provide those of ordinary skill in the art with a complete disclosure and description of how to make soluble proteins and carry out the methodology for finding such proteins, and are not intended to limit the scope of what is regarded as the invention. Efforts have been made to insure accuracy with respect to the numbers used (e.g. amounts, temperature, concentrations, etc.) but some experimental errors and deviations should be accounted for. Unless otherwise indicated, parts are parts by weight, molecular weight is weight average molecular weight, temperature is in degrees centigrade; and pressure is at or near atmospheric.

EXPERIMENTAL

Materials and Methods

Drugs and Chemicals. Doxorubicin (DOX) was obtained from Adria Laboratories (Columbus, Ohio), etoposide from Bristol-Myers (Evansville, Ind.), and vinblastine from Eli Lilly and Co. (Indianapolis, Ind.). PSC 833 was provided by Sandoz Pharmaceutical Corporation (Basel, Switzerland). Rhodamine-123 (Rh-123) was purchased from Molecular Probes (Eugene, Oreg.). All other anticancer agents were obtained from the National Cancer Institute, and all other chemicals from Sigma Chemical Co.

Cells and Tissue Culture. Details of the development and characterization of the human cell line MES-SA and its MDR variant MES-SA/Dx5 (Dx5), which were derived from sarcoma elements of a uterine mixed Mullerian tumor, are described in Harker and Sikic (1985) *Cancer Research* 45:3810–3815. MES-SA/DxP5002 (DxP) cells were derived from Dx5.05 cells (Dx5 cells selected and maintained at a DOX concentration of 0.5 $\mu$M) by step-wise selection in the presence of increasing DOX concentrations (from 40 nM up to 0.5 $\mu$M) and a constant PSC 833 concentration at 2 $\mu$M over a one-year period. Monolayer cultures of MES-SA cells and its variants were grown in McCoy's medium (Irvine Scientific, Santa Ana, Calif.) supplemented with 10% newborn calf serum (Gibco, Grand Island, N.Y.), 2 mM L-glutamine, and antibiotics(100 U/ml penicillin, 100 $\mu$g/ml streptomycin). Cells were maintained at 37° C. in a humidified atmosphere containing 5% $CO_2$ and manifested a plating efficiency of 85 %. DxP cell stocks were free from Mycoplasma infection as tested by the polymerase chain reaction (PCR) using primers for Mycoplasma DNA.

Cytogenetic Analysis and Fluorescence In situ Hybridization Metaphase chromosome preparations were examined for the presence and structure of chromosome 7, where the human mdr1 gene is normally located, by karyotyping and in situ hybridization with a chromosome 7 specific probe (Oncor, Inc., Gaithersburg, Md.). The hybridized chromosome was visualized by the method of Sasai et al. using fluorescence microscopy.

Growth Inhibition Assay. Approximately 8000 cells per well were seeded in 96 well plates and incubated with or without drugs for 72 hr at 37° C. in an atmosphere of 5% $CO_2$. Growth inhibition was evaluated by the MTT colorimetric assay in triplicate or quadruplicate as previously described. The absorbance was measured with a Thermo-Max microplate reader (Molecular Devices, Menlo Park, Calif.). The $IC_{50}$ (drug concentration resulting in 50% inhibition of MTT dye formation, compared to controls) was determined directly from semi-logarithmic dose-response curves. The doubling times of MES-SA, Dx5, and DxP were determined as previously described.

Reversal of MDR by Modulators. The modulation of resistance to DOX, paclitaxel, vinblastine, and etoposide was determined by MTT assays (as described above) in the presence of the MDR modulators PSC 833 (2 $\mu$M) or verapamil (6 $\mu$M). These concentrations of the modulators are non-cytotoxic and completely reverse resistance to DOX in cellular MDR models. The modulation ratio was obtained by comparing $IC_{50}$s in the presence and absence of modulators.

Cellular Accumulation of [$^{3}H$]-Daunorubicin, [$^{3}H$]-Vinblastine, and [$^{3}H$]Cyclosporine. lntracellular drug accumulation was quantified using radiolabeled drugs in a modified assay. The cells were seeded in 35×10 mm tissue culture dishes (Falcon, Becton Dickinson, Lincoln Park, N.J.), at $1 \times 10^6$ cells/dish. After overnight incubation, the growth medium was replaced with serum-free McCoy's 5A medium supplemented with 40 mM Hepes buffer (Sigma Chemicals, St. Louis, Mo.). Radiolabeled drugs were added at the appropriate concentration and incubated for 1 hr at 37° C. The medium was aspirated and cell pellet solubilized in 4%

SDS at 65° C. for 1 hr. Ecolite™ scintillation cocktail (INC Biochemicals, Costa Mesa, Calif.) was added and radioactivity determined on an LS-9000 scintillation counter (Beckman Instruments, Brea, Calif.). All values were normalized to protein content.

Flow Cytometric Analysis. The flow cytometric analysis of Rh-123 retention and P-gp expression were determined by a dual laser flow cytometer (FACS-II™; Becton Dickinson Corp., Mountain View, Calif.). Double labeling with Rh-123 and the monoclonal antibody UIC2 (Immunotech Coporation, Westbrook, Me.) was performed as previously described. Briefly, following the Rh-123 incubation step, cells were treated with UIC2 (40 $\mu$g/ml) and then reacted with either Texas Red or FITC-conjugated goat anti-mouse IgG2a secondary antibody (Caltag, So. San Francisco, Calif, ). Cells were centrifuged through a calf serum cushion, resuspended in 200 $\mu$l of modified ice-cold Hank's balanced salt solution, and analyzed by flow cytometry.

Amplimers used for rt-PCR. The oligonucleotides used as amplification primers (amplimers) in this study were synthesized by Operon Technologies (Alameda, Calif.) and Ana-Gen Inc. (Palo Alto, Calif.). The sets of amplimers specific for Topo II$\alpha$ and II$\beta$ protein and mrp have been previously described. A panel of mdr1 primers for mRNA sequence amplification was designed according to the published sequence. 28S Ribosomal cDNA was used as an endogenous control for PCR.

Reverse Transcriptase-Polymerase Chain Reaction (rt-PCR). The isolation of total RNA and procedures of rt-PCR were performed as previously reported. Samples were analyzed by 8% polyacrylamide gel electrophoresis in 89 mM Tris acetate, 2 mM disodium EDTA, pH 8.3 buffer, at 5V/cm. Gels were stained with ethidium bromide, and the desired products located on an ultraviolet transilluminator, photographed, and quantified using an Alpha Innotech IS 1000 image analyzer. PCR conditions for each pair of primers were determined by evaluating the linearity of the generation of PCR products with serial dilutions of cDNA (5, 25, 50 and 100 ng per reaction). Reactions were determined to be in the linear range of amplification by comparison of at least two dilutions of each sample and two cycle endpoints. All PCR experiments were performed on RNAs from several different preparations.

DNA Heteroduplex Analysis and PCR Sequencing mdr1 PCR products were subjected to heteroduplex analysis using the mutation detection enhancement system (J. T. Baker Inc. N.J.). An 8 to 12% MDE™ Gel (J. T. Baker Inc. N.J.) was used and stained with ethidium bromide, the desired products located on an ultraviolet transilluminator and photographed. The results were further assessed by DNA sequencing of the PCR products (Amersham Life Sci., Cleveland, Ohio). Sequences were obtained from several preparations of cDNA and these were compared with the parental cell line, D×5, and published human mdr1 sequence.

Genomic DNA PCR, Heteroduplex, Subcloning and Sequencing. In order to identify the presence of the mutation in genomic DNA of D×P cells, we isolated genomic DNA from MES-SA, D×5, and D×P cells. The PCR products were obtained by amplifying the target region using genomic specific primers located in introns 9 and 10, which are adjacent to exon 10 of mdr1: (SEQ ID NO:3) forward primer, 5'ATGGATCCTCTTCACATTCCTCAGGTAT-3', (SEQ ID NO:4) reverse primer, 5'CTCTCGAGGGCCAACTCAGACTTACATTAT-3' Heteroduplex analysis was performed and heteroduplex bands were subjected to PCR reamplification. The bands were purified from 8% polyacrylamide gel and subcloned into the pGEM-T vector (Promega). Individual clones were selected for sequencing.

Western blotting of P-gp and Topo II$\alpha$. Western blotting with chemiluminescent detection (ECL kit, Amersham Corp., Arlington Heights, Ill.) was used for the analysis of P-gp and Topo II$\alpha$proteins. Total cell lysates from the exponentially growing cells were used for P-gp immunoblotting, and a nuclear protein extract, prepared by the methods previously described, was utilized in the Topo II assay. Equal amounts of protein samples (20 $\mu$g ) were loaded on 8% SDS-polyacrylamidegels, and transferred onto Hybond™ nitrocellulose membranes (Amersham) using the semi-dry Sartoblot II® apparatus (Sartorius Filters Inc., Hayward, Calif.). The monoclonal antibodies anti-P-gp C219 (Signet Inc.) and anti-Topo II$\alpha$ (Topogen Inc.) were used as primary antibodies. Blots were exposed to a biotinylated goat anti-mouse antibody for 1 hr, followed by a streptavidin biotinylated horseradish peroxidase complex, which was then detected by ECE detection reagent. The membrane was exposed to Hyperfilm™ (Amersham) for autoradiography, and evaluated for the presence of P-gp and Topo II$\alpha$.

Immunohistochemical Analysis of P-gp and P110 Expression. Immunohistochemical analyses were performed using the monoclonal antibodies MRK16 and C219 for P-gp, and the antibody LRP-56 for the p110 major vault protein (Caltag, So. San Francisco, Calif.) as described previously.

Photoaffinity Labeling with [$^{25}$-I]-iodoarylazidoprazesin and [$^3$H]-Azidopine. Plasma membranes for photoaffinity labeling were prepared as described, followed by assays of displacement of the P-gp probes [$^{125}$I]-iodoarylazidoprazosin and [$^3$HI-azidopine. MES-SA, D×5, and D×P cells (100 $\mu$g protein) were incubated with [$^{125}$-I]-iodoarylazidoprazosin (81.4 TBq/mmol, NEN-Dupont, Boston, Mass.) and [$^3$H]-Azidopine (Amersham) in the presence or absence of modulators in a 10 mM Tris-HCI buffer (pH 7.4) at a final volume of 50 $\mu$l. These preparations were incubated at 25° C. for 1 hour in the dark, followed by a 20 min exposure to a 366 nm UV source (UVP, Inc., San Gabriel, Calif.). 50 $\mu$l of loading buffer was added and proteins separated on an 8% SDS-polyacrylamide gel, dried, and analyzed by autoradiography.

Clonal Analysis of D×P cells. Subcloning of cells was performed by limiting dilution. Both resistant and revertant clones were analyzed for the MDR phenotype, drug accumulation, and rt-PCR or heteroduplex as described above.

RESULTS

Establishment of the Doxorubicin and PSC Resistant Subline. Step-wise selection of the MDR human sarcoma cell line D×5 in the presence of increasing DOX concentrations and constant exposure to PSC 833 (2 $\eta$M) resulted, over a one-year period, in the stably DOX and PSC 833 resistant cell line, D×P. Karyotypic analysis revealed 47 or 48 chromosomes in both the D×5 and D×P cells with a similar G banding pattern of chromosome 7. Fluorescence in situ hybridization demonstrated two copies of chromosome 7 in both D×5 and D×P cells, whereas parental, drug sensitive MES-SA cells have 45 chromosomes and one chromosome 7.

Multidrug Resistance Phenotype. The drug resistance phenotype of D×P cells is shown in Table 1. Their level of resistance to the anthracycline DOX is similar to that of the parental D×5 cells, with a slightly decreased cross-resistance to daunorubicin. The most notable alterations were found in levels of resistance to dactinomycin and Vinca alkaloids.

Resistance to vinblastine decreased 17 fold, to vincristine 25 fold, and to vinorelbine 9 fold (to a level similar to that of drug sensitive MES-SA cells). Resistance to amsacrine decreased 13-fold, and sensitivity to ductinomycin was completely restored. This cell line maintained high levels of resistance to colchicine and paclitaxel (Taxol[R]), and moderately decreased resistance to podophyllotoxins(etoposide and teniposide). There was no significant difference in cellular generation time (22 hr) compared to parental Dx5 cells.

TABLE 1

The multidrug resistance phenotype of Dx5 and DxP cells.

| Cytotoxin | Fold Resistance[a] MES-SA | Dx5 | DxP | Dx5/DxP[b] |
|---|---|---|---|---|
| Anthracyclines | | | | |
| Daunorubicin | 1(20[c]) | 75 | 25 | 3 |
| Doxorubicin | 1(40) | 80 | 77 | 1 |
| Anti-microtubule | | | | |
| Colchicine | 1(1) | 79 | 75 | 1 |
| Paclitaxel | 1(1) | 175 | 100 | 2 |
| Vinblastine | 1(4) | 243 | 14 | 17 |
| Vincristine | 1(2) | 199 | 8 | 25 |
| vinorelbine | 1(60) | 17 | 2 | 9 |
| Epipodophyllotoxins | | | | |
| Etoposide | 1(500) | 42 | 17 | 2 |
| Teniposide | 1(100) | 135 | 53 | 3 |
| Others | | | | |
| D actinomycin | 1(0.3) | 183 | 1 | 183 |
| Amsacrine | 1(100) | 26 | 2 | 13 |

[a]Fold resistance was determined as described in the Experimental Procedures. Values are the means of at least three to six independent experiments.
[b]Fold of resistance difference in DxP cells compared with parental Dx5 cells.
[c]Values in parenthesis represent the $IC_{50}$'s of drug-sensitive MES-SA cells
nd, not determined.

In Vitro Modulation of MDR by PSC and Verapamil. Modulation of resistance to several MDR-related cytotoxins by PSC 833 (2 μM), cyclosporin (3 μM), and verapamil (6 μM) was examined by the MTT assay. PSC 833, the most potent of the modulators used, completely restored the sensitivity of the highly MDR cell line Dx5 to DOX, vinblastine, paclitaxel, vincristine and colchicine, relative to the drug sensitive MES-SA cells. In contrast, DxP cells were almost completely resistant to the modulating effects of PSC 833, substantially resistant to cyclosporin, and somewhat less resistant to modulation by verapamil (Table 2).

TABLE 2

Modulation of multidrug resistance in Dx5 and DxP cells

| Cytotoxin | MES-SA | Dx5 | DxP |
|---|---|---|---|
| Doxorubicin | 1 | 80 | 77 |
| +2 μM PSC 833 | 1 | 1 | 53 |
| +3 μM cyclosporin A | 0.5 | 2 | 30 |
| +6 μM Verapamil | 0.5 | 4 | 18 |
| Paclitaxel | 1 | 175 | 100 |
| +2 μM PSC 833 | 0.3–1[b] | 1 | 5 |
| +3 μM cyclosporin A | 0.5–1 | 13 | 38 |
| +6 [M Verapamil | 0.3–1 | 25 | 44 |
| Vinblastine | 1 | 243 | 14 |
| +2 μM PSC 833 | 0.3–1 | 1 | 12 |
| +3 μM cyclosporin A | 0.5–1 | 6 | 7 |
| +6 μM Verapamil | 0.4–1 | 4 | 3 |
| Vincristine | 1 | 199 | 8 |
| +2 μM PSC 833 | 0.7 | 1 | 7 |

TABLE 2-continued

Modulation of multidrug resistance in Dx5 and DxP cells

| Cytotoxin | MES-SA | Dx5 | DxP |
|---|---|---|---|
| +6 μM Verapamil | 0.3–1 | 7 | 3 |
| Colchicine | 1 | 79 | 75 |
| +2 μM PSC 833 | 1 | 1 | 70 |
| +3 μM cyclosporin A | 1 | 6 | 30 |
| +6 μM Verapamil | 1 | 12 | 30 |
| Etoposide | 1 | 42 | 18 |
| +2 μM PSC 833 | 1 | 1 | 18 |

[a]Fold resistance was determined as described in the Experimental Procedures.
[b]Increased sensitivity to cytotoxins was observed occasionally in MES-SA cells treated with MDR modulators, although these cells do not express mdr1.

Analysis of mdr1, Topo IIα and IIβ, and mrp Expression. Total RNA was extracted from isolated DxP clones and analyzed by rt-PCR for the presence of mdr1, Topo IIα, Topo IIβ, and mrp transcripts. In comparison to the parental Dx5 cells, DxP displayed levels of mdr1 transcripts similar to the parental Dx5 cells. The expression of mrp was compared with MES-SA and Dx5 cells, and normal human lung tissue as a positive control. A similar level of expression of mrp was observed in human lung tissue, MES-SA sarcoma cells, Dx5 and DxP cells. While no significant difference was seen in Topo IIα transcripts, DxP cells manifested a two fold elevation of Topo IIβ expression relative to Dx5 cells.

P-glycoprotein Expression. P-gp expression and function were analyzed by rt-PCR, immunoblotting with the C219 antibody, and flow cytometry with the antibody UIC2. Dx5 and DxP cells displayed similarly high levels of expression of P-gp. lmmunohistochemical staining of cells with the MRK16 and C219 antibodies confirmed that the expression of P-gp on DxP cells was predominantly localized to the plasma membrane and similar in amount to that observed in Dx5.

Topo IIα and p110 Expression. Expression of Topo IIα isoforms by immunoblotting revealed a slight increase in DxP compared to Dx5 cells. Neither Dx5 nor DxP cells had detectable expression of the p110 major vault protein, although the drug-sensitive MES-SA cells from which Dx5 cells were originally derived are weakly positive for p110.

Rh-123 Retention and Modulation with PSC. The cellular accumulation of the fluorescent P-gp substrate Rh-123 was markedly decreased in Dx5 cells, as expected for MDR cells. In contrast, DxP cells (although expressing abundant P-gp by UIC2 staining) manifested Rh-123 retention similar to the MDR-negative MES-SA cell line. PSC 833 (2 μM) completely restored Rh-123 accumulation in the DxS cell line, to levels similar to MES-SA and DxP cells.

[$^3$H]-Labeled drug Accumulation. Intracellular accumulations of [$^3$H]-daunorubicin, [$^3$H]-vinblastine, and [$^3$H]-cyclosporin were measured to compare the function of P-gp in Dx5 and DxP cells. Both Dx5 and DxP cells displayed similar decreases in [$^3$H]-daunorubicin accumulation, relative to the MES-SA cell line, while the accumulation of [$^3$H]-vinblastine was approximately 3 fold higher in DxP than Dx5 cells. The decreased drug accumulation in DxP cells was not modulated by PSC 833, whereas complete modulation was displayed by Dx5 cells. Uptake of [$^3$H]-cyclosporin was examined to assess the ability of P-gp to transport the cyclosporins. The intracellular concentration of cyclosporin in DxP cells was equal to that in MES-SA cells, and 2-fold higher than in Dx5 cells. The decreased accumulation of cyclosporin in D×5 cells was completely modulated by PSC 833 to the levels achieved in D×P and MES-SA cells.

Photoaffinity Labeling with [$^{251}$I]. Iodoarylazidoprazasin and [$^3$H]-Azidopine D×P cells displayed enhanced photoaffinity binding of P-gp by [$^{125}$I]-iodoarylazidoprazosin in the presence of 0.1 and 10 μM PSC 833 and vinblastine, in contrast to D×5 cells in which the photoaffinity labeling was effectively competed by PSC and vinblastine. The higher concentration (100 μM) of PSC 833 or vinblastine abolished detectable P-gp labeling by azidoprazosin in both cell lines. D×P cells were also resistant to the displacement by PSC or vinblastine of [$^3$H]-azidopine photoaffinity labeling. Verapamil was moderately active in both D×P and D×5 cells in displacing [$^3$H]-azidopine.

RT-PCR, DNA Heteroduplex Analysis, and MdrI DNA Sequencing. RT-PCR using primer sets spanning the P-gp coding sequences confirmed that the levels of expression of mdr1 were similar and that the PCR products showed no differences in size comparing the D×5 and D×P cells. DNA heteroduplex analysis revealed the formation of a heteroduplex with primers spanning nucleotides 1194 to 1519 of mdr1 cDNA, suggesting a sequence difference in transmembrane region 6 (TM6). Sequencing of this PCR product identified a deletion of base pairs 1427 to 1429 in this region, which encode the amino acid phenylalanine at position 335/336 of P-gp (Phe335/336). The PCR and sequencing results were reproduced in 4 different preparations of cDNA from D×P cells. The deletion of Phe335/336 is the only functional mutation in D×P cells compared with D×5 and the published human mdr1 sequence. There are other changes from the published mdr1 sequence which do not alter the P-gp amino acid sequence in D×P cells: from TCT (Ser) to TCC (Ser) in nucleotide 964, and from ATC (Ile) to ATT (Ile) in nucleotide 3859. These may be polymorphisms of P-gp since both D×P and D×5 have these same substitutions. Amino acid 185 was identified as Gly in both D×5 and D×P cells.

Identification of the 1427–1429 TTC Deletion in Genomic Sequence of D×P Cells. In order to identify the presence of the mutation in genomic DNA of D×P cells, genomic DNA was amplified using genomic specific primers of mdr1. Heteroduplex analysis was performed and revealed that a heteroduplex band existed in D×P but not D×5 cells. The TTC deletion at codon 335 was also verified by sequencing of the genomic PCR product. Thus, the one codon deletion was confirmed in D×P cells. A TTT deletion of codon 336 encodes the same amino acid product, as both positions are phenylalanine.

Subclonal Analysis of D×P cells. Single clones were obtained to analyze the genetic heterogeneity in D×P cells. As shown in Table 3, 11 isolated clones derived from D×P cells showed a similar phenotype including resistance to DOX, resistance to modulation by PSC, and a lower degree of resistance to vinblastine relative to parental D×5 cells. All tested clones expressed the mutant mdr1.

TABLE 3

Drug resistance phenotypes of subclones of DxP cells.

| Cells | DOX[a] | DOX + PSC | vinblastine | vinblastine + PSC | mdr1[b] |
|---|---|---|---|---|---|
| Controls | | | | | |
| MES-SA | 1 | 1 | 1 | 0.5 | Negative |

TABLE 3-continued

Drug resistance phenotypes of subclones of DxP cells.

| Cells | DOX[a] | DOX + PSC | vinblastine | vinblastine + PSC | mdr1[b] |
|---|---|---|---|---|---|
| Dx5 | 80 | 1 | 243 | 1 | wt |
| DxP | 77 | 53 | 14 | 12 | mut |
| Subclones[c] | | | | | |
| Dx/PAS | 163 | 51 | 15 | 5 | mut |
| Dx/PBS | 67 | 13 | 3 | 1 | nd |
| Dx/PCS | 50 | 23 | 8 | 3 | mut |
| Dx/PDS | 150 | 100 | 20 | 6 | mut |
| Dx/PES | 96 | 100 | 3 | 1 | mut |
| Dx/PFS | 150 | 75 | 21 | 8 | nd |
| Dx/PGS | 7 | 7 | 2 | 1 | nd |
| Dx/PHS | 83 | 37 | nd | nd | nd |
| Dx/PIS | 13 | 3 | 2 | 1 | mut |
| Dx/PJS | 175 | 75 | 19 | 10 | nd |
| Dx/PMS | 100 | 50 | 5 | 2 | mut |

[a]The numbers represent fold resistance relative to control, drug-sensitive MES-SA cells as determined by the MTT assay.
[b]Identification of mdr1 gene expression by RT-PCR and DNA heteroduplex assay. wt, wild type mdr1; mut, mutant mdr1 mRNA (deletion of the codon for aa335).
[c]Subclones of DxP were obtained by limiting dilution of cell populations in 96 well plates. The clones were maintained in drug free conditions over 2 months and were tested for their drug resistance phenotypes. nd, not determined.

The development of resistance to anticancer drugs is a major impediment to successful chemotherapy, and is often mediated by the membrane bound drug-efflux pump, P-gp. Substances which inhibit P-gp function and reverse the resistance phenotype in vitro, termed MDR modulators, have been developed with the intention of administering them in conjunction with MDR-related cytotoxins. The above results demonstrate the resistance mechanisms that arise in MDR cells during multistep selection with DOX, an MDR-substrate, and PSC 833, an effective modulator. A similar selection in non-MDR cells suppressed the activation of mdr1, and resulted in the emergence of mutants expressing alternative mechanisms of resistance, notably decreased expression of Topo IIα. Under the subject conditions of drug exposure, D×P cells displayed cross-resistance to several MDR-related drugs, including anthracyclines (DOX and daunorubicin), epipodophyllotoxins (etoposide and teniposide) and paclitaxel. However, D×P differed from the parental D×5 cells in their decreased resistance to Vinca alkaloids and lack of cross-resistance to dactinomycin (Table 1). Most notably, the MDR phenotype was not modulated by treatment with the P-gp inhibitor PSC 833 (Table 2).

Although overexpression of mdr1 is the best characterized mechanism of pleiotropic drug resistance, other mechanisms have been identified. Decreased expression or altered structure of Topo II have been observed in many models of resistance to epipodophyllotoxins, mitoxantrone, and anthracyclines such as DOX. A membrane ATPase of 190 kDa, distinct from P-gp, has been termed the multidrug resistance-associated protein, encoded by the mrp gene which has been cloned and sequenced in a DOX-selected lung cancer cell line. Under the subject experimental conditions, overexpression of the mrp mRNA or significant changes in Topo IIα and IIβ were not observed. D×P cells, like the parental D×5 cells, were not found to express the p110 major vault protein, recognized by the LRP-S6 antibody and associated with doxorubicin resistance in some cell models. The lack of an alternative resistance mechanism in D×P cells, the residual high expression of P-gp, and the pleiotropic nature of the resistance suggested that a mutant or modified P-gp with decreased affinity for cyclosporins was responsible for the phenotype of these cells.

The altered phenotype of D×P cells correlated very well with an altered functional activity of P-gp assessed by the cellular uptake of daunorubicin, vinblastine, and cyclosporine. D×P cells displayed a significant decrease in daunorubicin accumulation which was insensitive to modulation by PSC 833. These cells also exhibited increased vinblastine accumulation compared to D×5 cells, although the level of this drug was not as high as in drug-sensitive MES-SA cells and was not further increased by PSC 833. The accumulation of cyclosporin in D×P cells was equivalent to that of drug-sensitive MES-SA cells that do not express P-gp, strongly suggesting an altered affinity of the multidrug transporter for cyclosporins and consistent with the data that cyclosporine and its analog PSC did not modulate the MDR phenotype of D×P cells.

Compartmentalization or redistribution of P-gp leading to redistribution of cytotoxins may result in resistance to modulation. However, immunohistochemical experiments localized P-gp to the cell membrane in both D×5 and D×P. Furthermore, the same amount of P-gp expression and the existence of equivalent daunorubicin accumulation defects in the two cell lines demonstrated that P-gp in D×P cells was capable of transporting some substrates as well as the P-gp in D×5 cells. The P-gp's from the two cell lines have a similar electrophoretic mobility. Thus, a redistribution or marked structural change in the P-gp expressed in D×P cells were not evident.

The above results identify a novel mutation, consisting of a single codon deletion (Phe335) in the TM6 region of P-gp in D×P cells. The expression of this mutant P-gp in D×P cells is the result of selection of a spontaneously-arising mutant or selective allelic expression of an mdr1 gene which confers a PSC 833-resistant MDR phenotype. The mutation identified in this study provides insight into the relationship between P-gp structure and modulation of MDR by cyclosporins. The data indicate that a specific ligand-receptor mechanism is involved in P-gp mediated MDR. The deletion of Phe335 or 336 results in loss of the capacity to bind or transport cyclosporine, PSC 833, and vinblastine. The above data demonstrate that cyclosporine, PSC 833, vinblastine, Rh-123, and dactinomycin share at least one binding domain on P-gp. These results indicate that this residue plays an important role in the interaction of P-gp with cyclosporine and PSC 833.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated nucleic acid encoding mdr1ΔF335/336 protein, as other than an intact chromosome.

2. An isolated nucleic acid according to claim 1, having the nucleotide sequence of SEQ ID NO:1.

3. An expression cassette comprising a transcriptional initiation region, a nucleic acid according to claim 1 under the transcriptional regulation of said transcriptional initiation region, and a transcriptional termination region.

4. A cell comprising an expression cassette according to claim 3.

5. A cell according to claim 4, wherein said cell is a mammalian cell.

6. A cell according to claim 4, wherein said mammalian cell is human.

7. A cell according to claim 6, wherein said human cell is a hematopoietic stem cell.

8. A method for producing mdr1ΔF335/336 protein, said method comprising:

growing a cell according to claim 4, whereby said mdr1ΔF335/336 protein is expressed; and isolating said mdr1ΔF335/336 protein free of other proteins.

9. A purified polypeptide composition comprising at least 50 weight % of the protein present as mdr1ΔF335/336 protein.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 4264 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GAGCTCATTC  GAGTAGCGGC  TCTTCCAAGC  TCAAAGAAGC  AGAGGCCGCT  GTTCGTTTCC      60

TTTAGGTCTT  TCCACTAAAG  TCGGAGTATC  TTCTTCCAAG  ATTTCACGTC  TTGGTGGCCG     120

TTCCAAGGAG  CGCGAGGTCG  GGATGGATCT  TGAAGGGGAC  CGCAATGGAG  GAGCAAAGAA     180

GAAGAACTTT  TTTAAACTGA  ACAATAAAAG  TGAAAAAGAT  AAGAAGGAAA  AGAAACCAAC     240

TGTCAGTGTA  TTTTCAATGT  TTCGCTATTC  AAATTGCTTG  ACAAGTTGTA  TATGGTGGTG     300

GGAACTTTGG  CTGCCATCAT  CCATGGGGCT  GGACTTCCTC  TCATGATGCT  GGTGTTTGGA     360

GAAATGACAG  ATATCTTTGC  AAATGCAGGA  AATTTAGAAG  ATCTGATGTC  AAACATCACT     420

AATAGAAGTG  ATATCAATGA  TACAGGGTTC  TTCATGAATC  TGGAGGAAGA  CATGACCAGG     480

TATGCCTATT  ATTACAGTGG  AATTGGTGCT  GGGGTGCTGG  TTGCTGCTTA  CATTCAGGTT     540

TCATTTTGGT  GCCTGGCAGC  TGGAAGACAA  ATACACAAAA  TTAGAAAACA  GTTTTTTCAT     600
```

```
GCTATAATGC  GACAGGAGAT  AGGCTGGTTT  GATGTGCACG  ATGTTGGGGA  GCTTAACACC    660

CGACTTACAG  ATGATGTCTC  CAAGATTAAT  GAAGGAATTG  GTGACAAAAT  TGGAATGTTT    720

CAGTCAATGG  CAACATTTTT  CACTGGGTTT  ATAGTAGGAT  TTACACGTGG  TTGGAAGCTA    780

ACCCTTGTGA  TTTTGGCCAT  CAGTCCTGTT  CTTGGACTGT  CAGCTGCTGT  CTGGGCAAAG    840

ATACTATCTT  CATTACTGA   TAAAGAACTC  TTAGCGTATG  CAAAAGCTGG  AGCAGTAGCT    900

GAAGAGGTCT  TGGCAGCAAT  TAGAACTGTG  ATTGCATTTG  GAGGACAAAA  GAAAGAACTT    960

GAAAGGTACA  ACAAAAATTT  AGAAGAAGCT  AAAAGAATTG  GGATAAAGAA  AGCTATTACA   1020

GCCAATATTT  CTATAGGTGC  TGCTTTCCTG  CTGATCTATG  CATCTTATGC  TCTGGCCTTC   1080

TGGTATGGGA  CCACCTTGGT  CCTCTCAGGG  GAATATTCTA  TTGGACAAGT  ACTCACTGTA   1140

TTCTTTTCTG  TATTAATTGG  GGCTTTTAGT  GTTGGACAGG  CATCTCCAAG  CATTGAAGCA   1200

TTTGCAAATG  CAAGAGGAGC  AGCTTATGAA  ATCTTCAAGA  TAATTGATAA  TAAGCCAAGT   1260

ATTGACAGCT  ATTCGAAGAG  TGGGCACAAA  CCAGATAATA  TTAAGGGAAA  TTTGGAATTC   1320

AGAAATGTTC  ACTTCAGTTA  CCCATCTCGA  AAAGAAGTTA  AGATCTTGAA  GGGCCTGAAC   1380

CTGAAGGTGC  AGAGTGGGCA  GACGGTGGCC  CTGGTTGGAA  ACAGTGGCTG  TGGGAAGAGC   1440

ACAACAGTCC  AGCTGATGCA  GAGGCTCTAT  GACCCCACAG  AGGGGATGGT  CAGTGTTGAT   1500

GGACAGGATA  TTAGGACCAT  AAATGTAAGG  TTTCTACGGG  AAATCATTGG  TGTGGTGAGT   1560

CAGGAACCTG  TATTGTTTGC  CACCACGATA  GCTGAAAACA  TTCGCTATGG  CCGTGAAAAT   1620

GTCACCATGG  ATGAGATTGA  GAAAGCTGTC  AAGGAAGCCA  ATGCCTATGA  CTTTATCATG   1680

AAACTGCCTC  ATAAATTTGA  CACCCTGGTT  GGAGAGAGAG  GGGCCCAGTT  GAGTGGTGGG   1740

CAGAAGCAGA  GGATCGCCAT  TGCACGTGCC  CTGGTTCGCA  ACCCCAAGAT  CCTCCTGCTG   1800

GATGAGGCCA  CGTCAGCCTT  GGACACAGAA  AGCGAAGCAG  TGGTTCAGGT  GGCTCTGGAT   1860

AAGGCCAGAA  AAGGTCGGAC  CACCATTGTG  ATAGCTCATC  GTTTGTCTAC  AGTTCGTAAT   1920

GCTGACGTCA  TCGCTGGTTT  CGATGATGGA  GTCATTGTGG  AGAAAGGAAA  TCATGATGAA   1980

CTCATGAAAG  AGAAAGGCAT  TTACTTCAAA  CTTGTCACAA  TGCAGACAGC  AGGAAATGAA   2040

GTTGAATTAG  AAAATGCAGC  TGATGAATCC  AAAAGTGAAA  TTGATGCCTT  GGAAATGTCT   2100

TCAAATGATT  CAAGATCCAG  TCTAATAAGA  AAAAGATCAA  CTCGTAGGAG  TGTCCGTGGA   2160

TCACAAGCCC  AAGACAGAAA  GCTTAGTACC  AAAGAGGCTC  TGGATGAAAG  TATACCTCCA   2220

GTTTCCTTTT  GGAGGATTAT  GAAGCTAAAT  TTAACTGAAT  GGCCTTATTT  TGTTGTTGGT   2280

GTATTTTGTG  CCATTATAAA  TGGAGGCCTG  CAACCAGCAT  TTGCAATAAT  ATTTTCAAAG   2340

ATTATAGGGG  TTTTTACAAG  AATTGATGAT  CCTGAAACAA  AACGACAGAA  TAGTAACTTG   2400

TTTTCACTAT  TGTTTCTAGC  CCTTGGAATT  ATTTCTTTTA  TTACATTTTT  CCTTCAGGGT   2460

TTCACATTTG  GCAAAGCTGG  AGAGATCCTC  ACCAAGCGGC  TCCGATACAT  GGTTTTCCGA   2520

TCCATGCTCA  GACAGGATGT  GAGTTGGTTT  GATGACCCTA  AAAACACCAC  TGGAGCATTG   2580

ACTACCAGGC  TCGCCAATGA  TGCTGCTCAA  GTTAAAGGGG  CTATAGGTTC  CAGGCTTGCT   2640

GTAATTACCC  AGAATATAGC  AAATCTTGGG  ACAGGAATAA  TTATATCCTT  CATCTATGGT   2700

TGGCAACTAA  CACTGTTACT  CTTAGCAATT  GTACCCATCA  TTGCAATAGC  AGGAGTTGTT   2760

GAAATGAAAA  TGTTGTCTGG  ACAAGCACTG  AAAGATAAGA  AAGAACTAGA  AGGTGCTGGG   2820

AAGATCGCTA  CTGAAGCAAT  AGAAAACTTC  CGAACCGTTG  TTTCTTTGAC  TCAGGAGCAG   2880

AAGTTTGAAC  ATATGTATGC  TCAGAGTTTG  CAGGTACCAT  ACAGAAACTC  TTTGAGGAAA   2940

GCACACATCT  TTGGAATTAC  ATTTTCCTTC  ACCCAGGCAA  TGATGTATTT  TTCCTATGCT   3000
```

```
GGATGTTTCC  GGTTTGGAGC  CTACTTGGTG  GCACATAAAC  TCATGAGCTT  TGAGGATGTT    3060

CTGTTAGTAT  TTTCAGCTGT  TGTCTTTGGT  GCCATGGCCG  TGGGGCAAGT  CAGTTCATTT    3120

GCTCCTGACT  ATGCCAAAGC  CAAAATATCA  GCAGCCCACA  TCATCATGAT  CATTGAAAAA    3180

ACCCCTTTGA  TTGACAGCTA  CAGCACGGAA  GGCCTAATGC  CGAACACATT  GGAAGGAAAT    3240

GTCACATTTG  GTGAAGTTGT  ATTCAACTAT  CCCACCCGAC  CGGACATCCC  AGTGCTTCAG    3300

GGACTGAGCC  TGGAGGTGAA  GAAGGGCCAG  ACGCTGGCTC  TGGTGGGCAG  CAGTGGCTGT    3360

GGGAAGAGCA  CAGTGGTCCA  GCTCCTGGAG  CGGTTCTACG  ACCCCTTGGC  AGGGAAAGTG    3420

CTGCTTGATG  GCAAAGAAAT  AAAGCGACTG  AATGTTCAGT  GGCTCCGAGC  ACACCTGGGC    3480

ATCGTGTCCC  AGGAGCCCAT  CCTGTTTGAC  TGCAGCATTG  CTGAGAACAT  TGCCTATGGA    3540

GACAACAGCC  GGGTGGTGTC  ACAGGAAGAG  ATTGTGAGGG  CAGCAAGGA  GGCCAACATA     3600

CATGCCTTCA  TCGAGTCACT  GCCTAATAAA  TATAGCACTA  AAGTAGGAGA  CAAAGGAACT    3660

CAGCTCTCTG  GTGGCCAGAA  ACAACGCATT  GCCATAGCTC  GTGCCCTTGT  TAGACAGCCT    3720

CATATTTTGC  TTTTGGATGA  AGCCACGTCA  GCTCTGGATA  CAGAAAGTGA  AAAGGTTGTC    3780

CAAGAAGCCC  TGGACAAAGC  CAGAGAAGGC  CGCACCTGCA  TTGTGATTGC  TCACCGCCTG    3840

TCCACCATCC  AGAATGCAGA  CTTAATAGTG  GTGTTTCAGA  ATGGCAGAGT  CAAGGAGCAT    3900

GGCACGCATC  AGCAGCTGCT  GGCACAGAAA  GGCATCTATT  TTTCAATGGT  CAGTGTCCAG    3960

GCTGGAACAA  AGCGCCAGTG  AACTCTGACT  GTATGAGATG  TTAAATACTT  TTTAATATTT    4020

GTTTAGATAT  GACATTTATT  CAAAGTTAAA  AGCAAACACT  TACAGAATTA  TGAAGAGGTA    4080

TCTGTTTAAC  ATTTCCTCAG  TCAAGTTCAG  AGTCTTCAGA  GACTTCGTAA  TTAAAGGAAC    4140

AGAGTGAGAG  ACATCATCAA  GTGGAGAGAA  ATCATAGTTT  AAACTGCATT  ATAAATTTTA    4200

TAACAGAATT  AAAGTAGATT  TTAAAAGATA  AAATGTGTAA  TTTTGTTTAT  ATTTTCCCAT    4260

TTGG                                                                     4264
```

( 2 ) INFORMATION FOR SEQ ID NO:2:

( i ) SEQUENCE CHARACTERISTICS:
        ( A ) LENGTH: 1279 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Asp  Leu  Glu  Gly  Asp  Arg  Asn  Gly  Gly  Ala  Lys  Lys  Lys  Asn  Phe
  1              5                     10                         15

Phe  Lys  Leu  Asn  Asn  Lys  Ser  Glu  Lys  Asp  Lys  Lys  Glu  Lys  Lys  Pro
              20                     25                         30

Thr  Val  Ser  Val  Phe  Ser  Met  Phe  Arg  Tyr  Ser  Asn  Trp  Leu  Asp  Lys
              35                     40                         45

Leu  Tyr  Met  Val  Val  Gly  Thr  Leu  Ala  Ala  Ile  Ile  His  Gly  Ala  Gly
         50                         55                         60

Leu  Pro  Leu  Met  Met  Leu  Val  Phe  Gly  Glu  Met  Thr  Asp  Ile  Phe  Ala
 65                         70                         75                    80

Asn  Ala  Gly  Asn  Leu  Glu  Asp  Leu  Met  Ser  Asn  Ile  Thr  Asn  Arg  Ser
                   85                         90                        95

Asp  Ile  Asn  Asp  Thr  Gly  Phe  Phe  Met  Asn  Leu  Glu  Glu  Asp  Met  Thr
                  100                        105                       110

Arg  Tyr  Ala  Tyr  Tyr  Tyr  Ser  Gly  Ile  Gly  Ala  Gly  Val  Leu  Val  Ala
```

```
                            115                          120                          125
        Ala Tyr Ile Gln Val Ser Phe Trp Cys Leu Ala Ala Gly Arg Gln Ile
            130                         135                 140
        His Lys Ile Arg Lys Gln Phe Phe His Ala Ile Met Arg Gln Glu Ile
        145                     150                     155                 160
        Gly Trp Phe Asp Val His Asp Val Gly Glu Leu Asn Thr Arg Leu Thr
                            165                     170                 175
        Asp Asp Val Ser Lys Ile Asn Glu Val Ile Gly Asp Lys Ile Gly Met
                        180                     185                 190
        Phe Phe Gln Ser Met Ala Thr Phe Phe Thr Gly Phe Ile Val Gly Phe
                    195                     200                 205
        Thr Arg Gly Trp Lys Leu Thr Leu Val Ile Leu Ala Ile Ser Pro Val
            210                     215                 220
        Leu Gly Leu Ser Ala Ala Val Trp Ala Lys Ile Leu Ser Ser Phe Thr
        225                     230                 235                 240
        Asp Lys Glu Leu Leu Ala Tyr Ala Lys Ala Gly Ala Val Ala Glu Glu
                            245                 250                 255
        Val Leu Ala Ala Ile Arg Thr Val Ile Ala Phe Gly Gly Gln Lys Lys
                        260                 265                 270
        Glu Leu Glu Arg Tyr Asn Lys Asn Leu Glu Glu Ala Lys Arg Ile Gly
                    275                 280                 285
        Ile Lys Lys Ala Ile Thr Ala Asn Ile Ser Ile Gly Ala Ala Phe Leu
            290                 295                 300
        Leu Ile Tyr Ala Ser Tyr Ala Leu Ala Phe Trp Tyr Gly Thr Thr Leu
        305                 310                 315                     320
        Val Leu Ser Gly Glu Tyr Ser Ile Gly Gln Val Leu Thr Val Phe Ser
                        325                 330                 335
        Val Leu Ile Gly Ala Phe Ser Val Gly Gln Ala Ser Pro Ser Ile Glu
                    340                 345                 350
        Ala Phe Ala Asn Ala Arg Gly Ala Ala Tyr Glu Ile Phe Lys Ile Ile
                355                 360                 365
        Asp Asn Lys Pro Ser Ile Asp Ser Tyr Ser Lys Ser Gly His Lys Pro
            370                 375                 380
        Asp Asn Ile Lys Gly Asn Leu Glu Phe Arg Asn Val His Phe Ser Tyr
        385                 390                 395                     400
        Pro Ser Arg Lys Glu Val Lys Ile Leu Lys Gly Leu Asn Leu Lys Val
                        405                 410                 415
        Gln Ser Gly Gln Thr Val Ala Leu Val Gly Asn Ser Gly Cys Gly Lys
                    420                 425                 430
        Ser Thr Thr Val Gln Leu Met Gln Arg Leu Tyr Asp Pro Thr Glu Gly
                435                 440                 445
        Met Val Ser Val Asp Gly Gln Asp Ile Arg Thr Ile Asn Val Arg Phe
        450                 455                 460
        Leu Arg Glu Ile Ile Gly Val Val Ser Gln Glu Pro Val Leu Phe Ala
        465                     470                 475                 480
        Thr Thr Ile Ala Glu Asn Ile Arg Tyr Gly Arg Glu Asn Val Thr Met
                        485                 490                 495
        Asp Glu Ile Glu Lys Ala Val Lys Glu Ala Asn Ala Tyr Asp Phe Ile
                    500                 505                 510
        Met Lys Leu Pro His Lys Phe Asp Thr Leu Val Gly Glu Arg Gly Ala
                515                 520                 525
        Gln Leu Ser Gly Gly Gln Lys Gln Arg Ile Ala Ile Ala Arg Ala Leu
            530                 535                 540
```

```
Val  Arg  Asn  Pro  Lys  Ile  Leu  Leu  Leu  Asp  Glu  Ala  Thr  Ser  Ala  Leu
545                 550                      555                          560

Asp  Thr  Glu  Ser  Glu  Ala  Val  Val  Gln  Val  Ala  Leu  Asp  Lys  Ala  Arg
                    565                 570                     575

Lys  Gly  Arg  Thr  Thr  Ile  Val  Ile  His  Arg  Leu  Ser  Thr  Val  Arg
                    580                 585                     590

Asn  Ala  Asp  Val  Ile  Ala  Gly  Phe  Asp  Asp  Gly  Val  Ile  Val  Glu  Lys
               595                 600                     605

Gly  Asn  His  Asp  Glu  Leu  Met  Lys  Glu  Lys  Gly  Ile  Tyr  Phe  Lys  Leu
     610                      615                     620

Val  Thr  Met  Gln  Thr  Ala  Gly  Asn  Glu  Val  Glu  Leu  Glu  Asn  Ala  Ala
625                      630                 635                          640

Asp  Glu  Ser  Lys  Ser  Glu  Ile  Asp  Ala  Leu  Glu  Met  Ser  Ser  Asn  Asp
                    645                      650                          655

Ser  Arg  Ser  Ser  Leu  Ile  Arg  Lys  Arg  Ser  Thr  Arg  Arg  Ser  Val  Arg
               660                 665                     670

Gly  Ser  Gln  Ala  Gln  Asp  Arg  Lys  Leu  Ser  Thr  Lys  Glu  Ala  Leu  Asp
          675                 680                     685

Glu  Ser  Ile  Pro  Pro  Val  Ser  Phe  Trp  Arg  Ile  Met  Lys  Leu  Asn  Leu
     690                      695                     700

Thr  Glu  Trp  Pro  Tyr  Phe  Val  Val  Gly  Val  Phe  Cys  Ala  Ile  Ile  Asn
705                      710                     715                     720

Gly  Gly  Leu  Gln  Pro  Ala  Phe  Ala  Ile  Ile  Phe  Ser  Lys  Ile  Ile  Gly
                    725                      730                          735

Val  Phe  Thr  Arg  Ile  Asp  Asp  Pro  Glu  Thr  Lys  Arg  Gln  Asn  Ser  Asn
               740                 745                     750

Leu  Phe  Ser  Leu  Leu  Phe  Leu  Ala  Leu  Gly  Ile  Ile  Ser  Phe  Ile  Thr
          755                      760                     765

Phe  Phe  Leu  Gln  Gly  Phe  Thr  Phe  Gly  Lys  Ala  Gly  Glu  Ile  Leu  Thr
770                      775                     780

Lys  Arg  Leu  Arg  Tyr  Met  Val  Phe  Arg  Ser  Met  Leu  Arg  Gln  Asp  Val
785                 790                      795                          800

Ser  Trp  Phe  Asp  Asp  Pro  Lys  Asn  Thr  Thr  Gly  Ala  Leu  Thr  Thr  Arg
                    805                      810                          815

Leu  Ala  Asn  Asp  Ala  Ala  Gln  Val  Lys  Gly  Ala  Ile  Gly  Ser  Arg  Leu
                    820                      825                     830

Ala  Val  Ile  Thr  Gln  Asn  Ile  Ala  Asn  Leu  Gly  Thr  Gly  Ile  Ile  Ile
          835                      840                     845

Ser  Phe  Ile  Tyr  Gly  Trp  Gln  Leu  Thr  Leu  Leu  Leu  Leu  Ala  Ile  Val
     850                      855                     860

Pro  Ile  Ile  Ala  Ile  Ala  Gly  Val  Val  Glu  Met  Lys  Met  Leu  Ser  Gly
865                      870                     875                     880

Gln  Ala  Leu  Lys  Asp  Lys  Lys  Glu  Leu  Glu  Gly  Ala  Gly  Lys  Ile  Ala
                    885                      890                          895

Thr  Glu  Ala  Ile  Glu  Asn  Phe  Arg  Thr  Val  Val  Ser  Leu  Thr  Gln  Glu
               900                 905                     910

Gln  Lys  Phe  Glu  His  Met  Tyr  Ala  Gln  Ser  Leu  Gln  Val  Pro  Tyr  Arg
          915                      920                     925

Asn  Ser  Leu  Arg  Lys  Ala  His  Ile  Phe  Gly  Ile  Thr  Phe  Ser  Phe  Thr
     930                      935                     940

Gln  Ala  Met  Met  Tyr  Phe  Ser  Tyr  Ala  Gly  Cys  Phe  Arg  Phe  Gly  Ala
945                      950                     955                     960

Tyr  Leu  Val  Ala  His  Lys  Leu  Met  Ser  Phe  Glu  Asp  Val  Leu  Leu  Val
               965                      970                          975
```

| | | | | | | | | | | | | | | |
|---|---|---|---|---|---|---|---|---|---|---|---|---|---|---|
|Phe|Ser|Ala|Val 980|Val|Phe|Gly|Ala|Met 985|Ala|Val|Gly|Gln 990|Val|Ser|Ser|
|Phe|Ala|Pro 995|Asp|Tyr|Ala|Lys|Ala 1000|Lys|Ile|Ser|Ala|Ala 1005|His|Ile|Ile|
|Met|Ile 1010|Ile|Glu|Lys|Thr|Pro 1015|Leu|Ile|Asp|Ser|Tyr 1020|Ser|Thr|Glu|Gly|
|Leu 1025|Met|Pro|Asn|Thr|Leu 1030|Glu|Gly|Asn|Val|Thr 1035|Phe|Gly|Glu|Val|Val 1040|
|Phe|Asn|Tyr|Pro 1045|Thr|Arg|Pro|Asp|Ile 1050|Pro|Val|Leu|Gln|Gly 1055|Leu|Ser|
|Leu|Glu|Val|Lys 1060|Lys|Gly|Gln|Thr|Leu 1065|Ala|Leu|Val|Gly 1070|Ser|Ser|Gly|
|Cys|Gly|Lys 1075|Ser|Thr|Val|Val|Gln 1080|Leu|Leu|Glu|Arg|Phe 1085|Tyr|Asp|Pro|
|Leu|Ala|Gly|Lys 1090|Val|Leu|Leu|Asp 1095|Gly|Lys|Glu|Ile|Lys 1100|Arg|Leu|Asn|
|Val 1105|Gln|Trp|Leu|Arg|Ala 1110|His|Leu|Gly|Ile|Val 1115|Ser|Gln|Glu|Pro|Ile 1120|
|Leu|Phe|Asp|Cys|Ser 1125|Ile|Ala|Glu|Asn|Ile 1130|Ala|Tyr|Gly|Asp|Asn 1135|Ser|
|Arg|Val|Val|Ser 1140|Gln|Glu|Glu|Ile|Val 1145|Arg|Ala|Ala|Lys|Glu 1150|Ala|Asn|
|Ile|His|Ala 1155|Phe|Ile|Glu|Ser|Leu 1160|Pro|Asn|Lys|Tyr|Ser 1165|Thr|Lys|Val|
|Gly|Asp|Lys 1170|Gly|Thr|Gln|Leu|Ser 1175|Gly|Gly|Gln|Lys|Gln 1180|Arg|Ile|Ala|
|Ile 1185|Ala|Arg|Ala|Leu|Val 1190|Arg|Gln|Pro|His|Ile 1195|Leu|Leu|Leu|Asp|Glu 1200|
|Ala|Thr|Ser|Ala|Leu 1205|Asp|Thr|Glu|Ser|Glu 1210|Lys|Val|Val|Gln|Glu 1215|Ala|
|Leu|Asp|Lys|Ala 1220|Arg|Glu|Gly|Arg|Thr 1225|Cys|Ile|Val|Ile|Ala 1230|His|Arg|
|Leu|Ser|Thr 1235|Ile|Gln|Asn|Ala|Asp 1240|Leu|Ile|Val|Val|Phe 1245|Gln|Asn|Gly|
|Arg|Val|Lys 1250|Glu|His|Gly|Thr|His 1255|Gln|Gln|Leu|Leu|Ala 1260|Gln|Lys|Gly|
|Ile 1265|Tyr|Phe|Ser|Met|Val 1270|Ser|Val|Gln|Ala|Gly 1275|Thr|Lys|Arg|Gln|

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATGGATCCTC TTCACATTCC TCAGGTAT          28

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:4:

| CTCTCGAGGG | CCAACTCAGA | CTTACATTAT | | | | 30 |

(2) INFORMATION FOR SEQ ID NO:5:

(i) SEQUENCE CHARACTERISTICS:
(A) LENGTH: 4264 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

| GAGCTCATTC | GAGTAGCGGC | TCTTCCAAGC | TCAAAGAAGC | AGAGGCCGCT | GTTCGTTTCC | 60 |
| TTTAGGTCTT | TCCACTAAAG | TCGGAGTATC | TTCTTCCAAG | ATTTCACGTC | TTGGTGGCCG | 120 |
| TTCCAAGGAG | CGCGAGGTCG | GGATGGATCT | TGAAGGGGAC | CGCAATGGAG | GAGCAAAGAA | 180 |
| GAAGAACTTT | TTTAAACTGA | ACAATAAAAG | TGAAAAAGAT | AAGAAGGAAA | AGAAACCAAC | 240 |
| TGTCAGTGTA | TTTTCAATGT | TCGCTATTC | AAATTGCTTG | ACAAGTTGTA | TATGGTGGTG | 300 |
| GGAACTTTGG | CTGCCATCAT | CCATGGGGCT | GGACTTCCTC | TCATGATGCT | GGTGTTTGGA | 360 |
| GAAATGACAG | ATATCTTTGC | AAATGCAGGA | AATTTAGAAG | ATCTGATGTC | AAACATCACT | 420 |
| AATAGAAGTG | ATATCAATGA | TACAGGGTTC | TTCATGAATC | TGGAGGAAGA | CATGACCAGG | 480 |
| TATGCCTATT | ATTACAGTGG | AATTGGTGCT | GGGGTGCTGG | TTGCTGCTTA | CATTCAGGTT | 540 |
| TCATTTTGGT | GCCTGGCAGC | TGGAAGACAA | ATACACAAAA | TTAGAAAACA | GTTTTTTCAT | 600 |
| GCTATAATGC | GACAGGAGAT | AGGCTGGTTT | GATGTGCACG | ATGTTGGGGA | GCTTAACACC | 660 |
| CGACTTACAG | ATGATGTCTC | CAAGATTAAT | GAAGGAATTG | GTGACAAAAT | TGGAATGTTC | 720 |
| CAGTCAATGG | CAACATTTTT | CACTGGGTTT | ATAGTAGGAT | TTACACGTGG | TTGGAAGCTA | 780 |
| ACCCTTGTGA | TTTTGGCCAT | CAGTCCTGTT | CTTGGACTGT | CAGCTGCTGT | CTGGGCAAAG | 840 |
| ATACTATCTT | CATTTACTGA | TAAAGAACTC | TTAGCGTATG | CAAAAGCTGG | AGCAGTAGCT | 900 |
| GAAGAGGTCT | TGGCAGCAAT | TAGAACTGTG | ATTGCATTTG | GAGGACAAAA | GAAAGAACTT | 960 |
| GAAAGGTACA | ACAAAAATTT | AGAAGAAGCT | AAAAGAATTG | GGATAAAGAA | AGCTATTACA | 1020 |
| GCCAATATTT | CTATAGGTGC | TGCTTTCCTG | CTGATCTATG | CATCTTATGC | TCTGGCCTTC | 1080 |
| TGGTATGGGA | CCACCTTGGT | CCTCTCAGGG | GAATATTCTA | TTGGACAAGT | ACTCACTGTA | 1140 |
| TTCTTTTCTG | TATTAATTGG | GGCTTTTAGT | GTTGGACAGG | CATCTCCAAG | CATTGAAGCA | 1200 |
| TTTGCAAATG | CAAGAGGAGC | AGCTTATGAA | ATCTTCAAGA | TAATTGATAA | TAAGCCAAGT | 1260 |
| ATTGACAGCT | ATTCGAAGAG | TGGGCACAAA | CCAGATAATA | TTAAGGGAAA | TTTGGAATTC | 1320 |
| AGAAATGTTC | ACTTCAGTTA | CCCATCTCGA | AAAGAAGTTA | AGATCTTGAA | GGGCCTGAAC | 1380 |
| CTGAAGGTGC | AGAGTGGGCA | GACGGTGGCC | CTGGTTGGAA | ACAGTGGCTG | TGGGAAGAGC | 1440 |
| ACAACAGTCC | AGCTGATGCA | GAGGCTCTAT | GACCCCACAG | AGGGGATGGT | CAGTGTTGAT | 1500 |
| GGACAGGATA | TTAGGACCAT | AAATGTAAGG | TTTCTACGGG | AAATCATTGG | TGTGGTGAGT | 1560 |
| CAGGAACCTG | TATTGTTTGC | CACCACGATA | GCTGAAAACA | TTCGCTATGG | CCGTGAAAAT | 1620 |
| GTCACCATGG | ATGAGATTGA | GAAAGCTGTC | AAGGAAGCCA | ATGCCTATGA | CTTTATCATG | 1680 |
| AAACTGCCTC | ATAAATTTGA | CACCCTGGTT | GGAGAGAGAG | GGGCCCAGTT | GAGTGGTGGG | 1740 |
| CAGAAGCAGA | GGATCGCCAT | TGCACGTGCC | CTGGTTCGCA | ACCCCAAGAT | CCTCCTGCTG | 1800 |

```
GATGAGGCCA  CGTCAGCCTT  GGACACAGAA  AGCGAAGCAG  TGGTTCAGGT  GGCTCTGGAT   1860

AAGGCCAGAA  AAGGTCGGAC  CACCATTGTG  ATAGCTCATC  GTTTGTCTAC  AGTTCGTAAT   1920

GCTGACGTCA  TCGCTGGTTT  CGATGATGGA  GTCATTGTGG  AGAAAGGAAA  TCATGATGAA   1980

CTCATGAAAG  AGAAAGGCAT  TTACTTCAAA  CTTGTCACAA  TGCAGACAGC  AGGAAATGAA   2040

GTTGAATTAG  AAAATGCAGC  TGATGAATCC  AAAAGTGAAA  TTGATGCCTT  GGAAATGTCT   2100

TCAAATGATT  CAAGATCCAG  TCTAATAAGA  AAAGATCAA   CTCGTAGGAG  TGTCCGTGGA   2160

TCACAAGCCC  AAGACAGAAA  GCTTAGTACC  AAAGAGGCTC  TGGATGAAAG  TATACCTCCA   2220

GTTTCCTTTT  GGAGGATTAT  GAAGCTAAAT  TTAACTGAAT  GGCCTTATTT  TGTTGTTGGT   2280

GTATTTGTG   CCATTATAAA  TGGAGGCCTG  CAACCAGCAT  TTGCAATAAT  ATTTTCAAAG   2340

ATTATAGGGG  TTTTACAAG   AATTGATGAT  CCTGAAACAA  AACGACAGAA  TAGTAACTTG   2400

TTTTCACTAT  TGTTTCTAGC  CCTTGGAATT  ATTTCTTTTA  TTACATTTTT  CCTTCAGGGT   2460

TTCACATTTG  GCAAAGCTGG  AGAGATCCTC  ACCAAGCGGC  TCCGATACAT  GGTTTTCCGA   2520

TCCATGCTCA  GACAGGATGT  GAGTTGGTTT  GATGACCCTA  AAAACACCAC  TGGAGCATTG   2580

ACTACCAGGC  TCGCCAATGA  TGCTGCTCAA  GTTAAAGGGG  CTATAGGTTC  CAGGCTTGCT   2640

GTAATTACCC  AGAATATAGC  AAATCTTGGG  ACAGGAATAA  TTATATCCTT  CATCTATGGT   2700

TGGCAACTAA  CACTGTTACT  CTTAGCAATT  GTACCCATCA  TTGCAATAGC  AGGAGTTGTT   2760

GAAATGAAAA  TGTTGTCTGG  ACAAGCACTG  AAAGATAAGA  AAGAACTAGA  AGGTGCTGGG   2820

AAGATCGCTA  CTGAAGCAAT  AGAAAACTTC  CGAACCGTTG  TTTCTTTGAC  TCAGGAGCAG   2880

AAGTTTGAAC  ATATGTATGC  TCAGAGTTTG  CAGGTACCAT  ACAGAAACTC  TTTGAGGAAA   2940

GCACACATCT  TTGGAATTAC  ATTTTCCTTC  ACCCAGGCAA  TGATGTATTT  TTCCTATGCT   3000

GGATGTTTCC  GGTTTGGAGC  CTACTTGGTG  GCACATAAAC  TCATGAGCTT  TGAGGATGTT   3060

CTGTTAGTAT  TTTCAGCTGT  TGTCTTTGGT  GCCATGGCCG  TGGGGCAAGT  CAGTTCATTT   3120

GCTCCTGACT  ATGCCAAAGC  CAAAATATCA  GCAGCCCACA  TCATCATGAT  CATTGAAAAA   3180

ACCCCTTTGA  TTGACAGCTA  CAGCACGGAA  GGCCTAATGC  CGAACACATT  GGAAGGAAAT   3240

GTCACATTTG  GTGAAGTTGT  ATTCAACTAT  CCCACCCGAC  CGGACATCCC  AGTGCTTCAG   3300

GGACTGAGCC  TGGAGGTGAA  GAAGGGCCAG  ACGCTGGCTC  TGGTGGGCAG  CAGTGGCTGT   3360

GGGAAGAGCA  CAGTGGTCCA  GCTCCTGGAG  CGGTTCTACG  ACCCCTTGGC  AGGGAAAGTG   3420

CTGCTTGATG  GCAAAGAAAT  AAAGCGACTG  AATGTTCAGT  GGCTCCGAGC  ACACCTGGGC   3480

ATCGTGTCCC  AGGAGCCCAT  CCTGTTTGAC  TGCAGCATTG  CTGAGAACAT  TGCCTATGGA   3540

GACAACAGCC  GGGTGGTGTC  ACAGGAAGAG  ATTGTGAGGG  CAGCAAAGGA  GGCCAACATA   3600

CATGCCTTCA  TCGAGTCACT  GCCTAATAAA  TATAGCACTA  AGTAGGAGA   CAAAGGAACT   3660

CAGCTCTCTG  GTGGCCAGAA  ACAACGCATT  GCCATAGCTC  GTGCCCTTGT  TAGACAGCCT   3720

CATATTTTGC  TTTTGGATGA  AGCCACGTCA  GCTCTGGATA  CAGAAAGTGA  AAAGGTTGTC   3780

CAAGAAGCCC  TGGACAAAGC  CAGAGAAGGC  CGCACCTGCA  TTGTGATTGC  TCACCGCCTG   3840

TCCACCATCC  AGAATGCAGA  CTTAATAGTG  GTGTTTCAGA  ATGGCAGAGT  CAAGGAGCAT   3900

GGCACGCATC  AGCAGCTGCT  GGCACAGAAA  GGCATCTATT  TTTCAATGGT  CAGTGTCCAG   3960

GCTGGAACAA  AGCGCCAGTG  AACTCTGACT  GTATGAGATG  TTAAATACTT  TTTAATATTT   4020

GTTTAGATAT  GACATTTATT  CAAAGTTAAA  AGCAAACACT  TACAGAATTA  TGAAGAGGTA   4080

TCTGTTTAAC  ATTTCCTCAG  TCAAGTTCAG  AGTCTTCAGA  GACTTCGTAA  TTAAAGGAAC   4140

AGAGTGAGAG  ACATCATCAA  GTGGAGAGAA  ATCATAGTTT  AAACTGCATT  ATAAATTTTA   4200
```

```
TAACAGAATT AAAGTAGATT TTAAAAGATA AAATGTGTAA TTTTGTTTAT ATTTTCCCAT    4260

TTGG                                                                 4264
```